(12) United States Patent
Smith et al.

(10) Patent No.: US 7,348,974 B2
(45) Date of Patent: Mar. 25, 2008

(54) IMAGE PROCESSING SYSTEM FOR USE WITH A PATIENT POSITIONING DEVICE

(75) Inventors: Norman Ronald Smith, London (GB); Ivan Daniel Meir, London (GB)

(73) Assignee: Vision RT Limited (GB)

( * ) Notice: Subject to any disclaimer, the term of this patent is extended or adjusted under 35 U.S.C. 154(b) by 42 days.

(21) Appl. No.: 11/234,533

(22) Filed: Sep. 23, 2005

(65) Prior Publication Data

US 2006/0079757 A1    Apr. 13, 2006

(51) Int. Cl.
G06T 15/00    (2006.01)

(52) U.S. Cl. ............ 345/420; 378/57; 382/152

(58) Field of Classification Search ........ 345/419, 345/581, 423, 428, 420; 378/57, 62, 64; 382/152; 348/362
See application file for complete search history.

(56) References Cited

U.S. PATENT DOCUMENTS

| | | | | |
|---|---|---|---|---|
| 5,315,630 | A | 5/1994 | Sturm et al. ............... 378/65 |
| 5,347,462 | A | 9/1994 | Okuda et al. ......... 364/999.999 |
| 5,655,030 | A | 8/1997 | Suzuki ..................... 382/152 |
| 5,696,838 | A | 12/1997 | Chiu et al. ................ 235/492 |
| 6,516,046 | B1 | 2/2003 | Frohlich et al. ............. 378/65 |
| 6,724,393 | B2 * | 4/2004 | Perry et al. ................ 345/581 |
| 6,816,200 | B1 | 11/2004 | Gough ..................... 348/362 |
| 7,034,818 | B2 * | 4/2006 | Perry et al. ................ 345/419 |
| 2002/0032550 | A1 | 3/2002 | Ward et al. ................. 703/10 |
| 2002/0164077 | A1 | 11/2002 | Lee et al. .................. 382/224 |

FOREIGN PATENT DOCUMENTS

| | | |
|---|---|---|
| DE | 19728788 | 1/1999 |
| EP | 0364614 | 4/1990 |
| EP | 0501716 | 9/1992 |
| JP | 08237543 | 9/1996 |
| JP | 9010204 | 1/1997 |
| JP | 11166818 | 6/1999 |
| JP | 2005027154 | 1/2005 |
| WO | 9927839 | 6/1999 |
| WO | 0174268 | 10/2001 |
| WO | 2004004828 | 1/2004 |

\* cited by examiner

*Primary Examiner*—Phu K. Nguyen
(74) *Attorney, Agent, or Firm*—Fogg & Powers LLC

(57) ABSTRACT

An image processing system (1-5) is provided which obtains images of a patient (8) from multiple view points and which then generates positioning instructions for a mechanical couch (7) to vary the position of a patient. A number of techniques are disclosed in order to calibrate the image processing system so as to enable the image processing system to identify the iso center of radiation beams generated by a treatment apparatus (6). Techniques for processing generated 3 dimensional models to monitor a patient's breathing are also disclosed.

18 Claims, 11 Drawing Sheets

IMAGE PROCESSING SYSTEM FOR USE WITH A PATIENT POSITIONING DEVICE

BACKGROUND TO THE INVENTION

1. Field of the Invention

The present invention relates to image processing. More particularly, embodiments of the present invention relate to image processing systems for use with patient positioning devices.

2. Description of the Related Art

One application of the present invention is in the field of radiotherapy. Radiotherapy consists of projecting onto a predetermined region of a patient=s body, a radiation beam so as to destroy or eliminate tumours existing therein. Such treatment is usually carried out periodically and repeatedly. At each medical intervention, the radiation source must be positioned with respect to the patient in order to irradiate the selected region with the highest possible accuracy to avoid radiating adjacent tissue on which radiation beams would be harmful.

A fundamental problem with radiotherapy is the need to position the patient in the same position, when obtaining diagnostic images and each of the subsequent times when radiation is applied to the patient=s body. Present systems for positioning patients include various forms of systems for placing markers on the patient to enable the patient to be realigned for different applications of therapy.

Thus for example U.S. Pat. No. 5,954,647 discloses the use of a specially moulded bite plate on which LED=s are placed to enable the head of an individual to be orientated in the same position in which diagnostic images are obtained. Similarly U.S. Pat. No. 5,446,548 describes another positioning and monitoring system. The system of U.S. Pat. No. 5,446,548 involves the fixing of infra-red reflective markers on parts of a patient=s body.

Although known systems involving the tracking of markers fixed relative to the patient enable the patient=s positioning to be monitored, it is desirable to be able to determine the patient=s position more accurately to increase the effectiveness of treatment. Further, it is desirable to provide a positioning system which minimises the extra time required and the inconvenience to a patient arising from placing or fixing markers and thus reduces the stresses placed upon the patient during treatment.

To that end Vision RT Limited have developed a patient positioning system in which a three dimensional model of the surface of the patient is generated utilising a number of stereoscopic video images of the patient. The video images are processed to generate a three dimensional model which is rapidly updated to account for movement and any changes in the position of the patient. This patient positioning system is described in detail in Vision RT Limited's co-pending U.S. patent application Ser. No. 10/516400 which is hereby incorporated by reference. It is however, desirable to improve further the accuracy with which three dimensional models of patients can be generated and utilised to position a patient relative to a therapeutic apparatus such as a radio therapy apparatus.

SUMMARY OF THE INVENTION

In accordance with one aspect of the present invention there is provided method and apparatus for modelling the intersection of a wire mesh model with a plane.

In another aspect of the present invention there is provided apparatus and method for determining a transformation necessary to transform an image of a calibration sheet obtained by a camera to represent an image of the sheet from a predetermined position.

In accordance with a further aspect of the present invention there is provided apparatus and method for identifying the relative positions of one or more cameras relative to the iso-centre of a treatment apparatus.

In another aspect of the present invention there is provided apparatus and method for determining exposure settings for a patient monitoring system.

In a further aspect of the present invention there is provided apparatus and method for generating in control instructions for a mechanical couch operable to be moved vertically, laterally and operable to be rotated about a predetermined axis.

BRIEF DESCRIPTION OF THE DRAWINGS

An embodiment of the present invention will now be described with reference to the accompanying drawings in which.

DETAILED DESCRIPTION OF THE PREFERRED EMBODIMENT

Patient Positioning System

Figure 1:
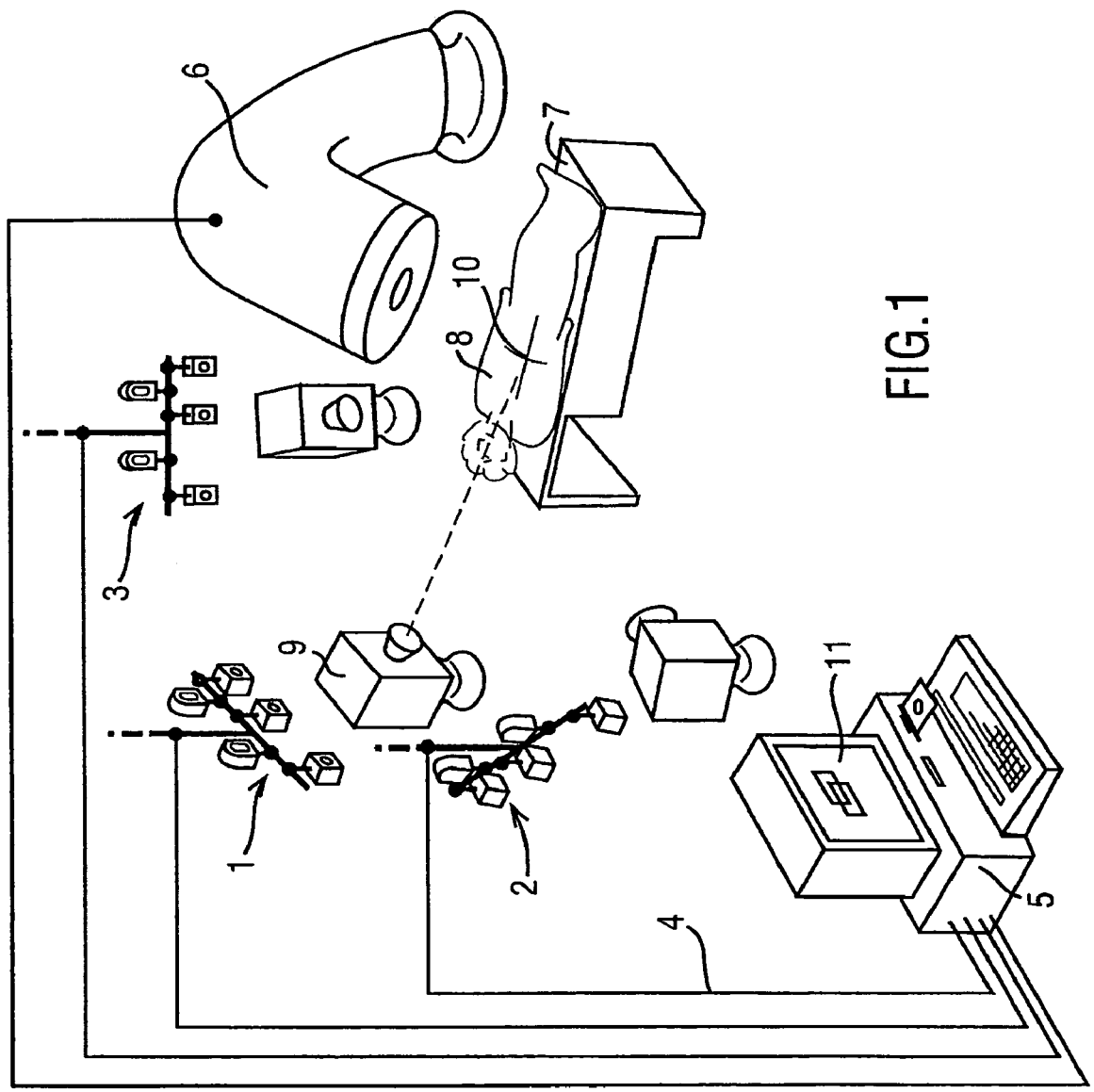
FIG. 1 is a schematic diagram of a patient positioning system in accordance with an embodiment of the present invention.

FIG. 1 is a schematic diagram of a patient positioning system in accordance with an embodiment of the present invention. In accordance with this embodiment, there is provided a set of three camera rigs 1, 2, 3 that are connected by wiring 4 to a computer 5. The computer 5 is also connected to treatment apparatus 6 such as a linear accelerator for applying radiotherapy or an x-ray simulator for planning radiotherapy. A mechanical couch 7 is provided as part of the treatment apparatus 6 upon which a patient 8 lies during treatment. The treatment apparatus 6 and the mechanical couch 7 are arranged such that under the control of the computer 5 the relative positions of the mechanical couch 7 and the treatment apparatus 6 may be varied, laterally, vertically, longitudinally and rotationally. Also provided as part of the system is a laser projection apparatus 9 which is arranged to project three laser beams 10 onto the body of a patient 8 lying on the mechanical couch 7 where the three laser beams 10 are such to project planes of light which collectively identify the focussing point of the radiation generated by the treatment apparatus 6.

In use, the cameras of the camera rigs 1, 2, 3 obtain video images of a patient 8 lying on the mechanical couch 7. These video images are passed via the wiring 4 to the computer 5. The computer 5 then processes the images to generate a three-dimensional model of the surface of the patient, which is displayed on the screen 11 of the computer 5. This processing is described in detail in WO 2004/004828 which has previously been incorporated by reference. The three-dimensional model of the patient is then continually updated utilising the stream of video images obtained from the cameras of the camera rigs 1, 2, 3. The three-dimensional models of the surface of a patient 8 are also utilised by the computer 5 to control the treatment apparatus 6 to position the mechanical couch 7 relative to the treatment apparatus 6 in a consistent manner throughout the course of a treatment.

Figure 2:
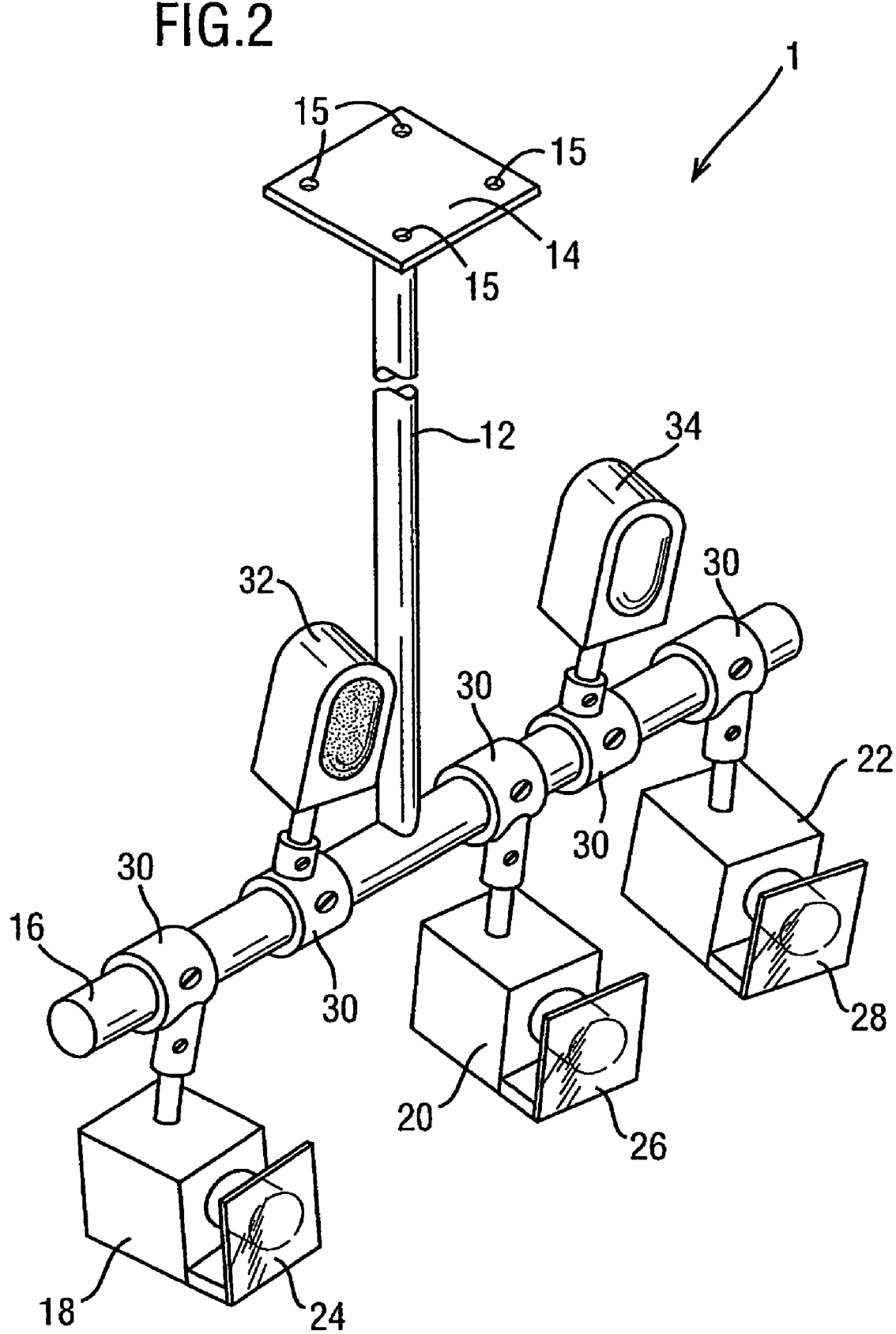
FIG. 2 is a perspective view of a camera rig of the patient positioning system of FIG. 1.

FIG. 2 is a schematic illustration of one of the set of camera rigs 1, 2, 3 of this embodiment of the present invention. All of the camera rigs 1, 2, 3 in this embodiment are identical to the others with the three camera rigs 1, 2, 3 being arranged with one either side of the mechanical couch 7 and one at the head of the mechanical couch 7. The arrangement of cameras of the rigs 1, 2, 3 are such that all the cameras of the camera rigs view substantially the same portion of the patient immediately beneath the treatment apparatus 6 so that a complete model of that portion of the patient 8 can be generated.

The camera rigs 1, 2, 3 each comprise a T-bar 12 which is suspended from the roof of the room within which the treatment apparatus 6 is provided. To this end a base plate is provided at the top of the T-bar 12 with the main body of the T-bar 12 extending down from the centre of this base plate. Provided in each of the corners of the base plate 14 are fixing holes 15 through which bolts pass to fix the T-bar 12 in position in the room containing the treatment apparatus 6.

Provided at the opposite end of the T-bar 12 to the base plate 14 attached to the horizontal cross bar 16 forming the T-section of the T-bar are three cameras 18, 20, 22. These cameras 18, 20, 22 are arranged along the cross bar 16, and in order from left to right along the cross bar 16 are a first geometry camera 18, a texture camera 20 and a second geometry camera 22. The cameras 18, 20, 22 each comprise monochrome analogue video cameras such as the Pulnix PE100.

Provided in front of the lenses of each of the cameras are filters 24, 26, 28. The filters on the two geometry cameras 18, 22 are arranged to prevent the geometry cameras 18, 22 from receiving light having a wavelength below 570 nm. The filter 26 in front of the lens of the texture camera 20 comprises a filter preventing the texture camera 20 from receiving light with a wavelength greater than 540 nm.

Each of the cameras 18, 20, 22 is attached to the horizontal bar 16 of the T-bar 12 by a clamp 30 which attaches the cameras 18, 20, 22 to the horizontal cross bar 16 of the T-bar 12, whilst permitting the orientation of the cameras 18, 20, 22 relative to the horizontal bar 16 of the T-bar 12 to be adjusted.

Also attached to the horizontal bar 16 of the T-bar 12 by further clamps 30 are a first 32 and second 34 light source. In this embodiment the first light 32 source comprises a light source arranged to irradiate light having a wavelength greater than 570 nm and being arranged to project onto the surface of a patient 8 lying on the mechanical couch 7 of the treatment apparatus 6 a random speckle pattern. An example of a suitable light source would be a slide and slide projector, where the slide bears a non-repeating speckle pattern and the slide projector comprises a filtered light source filtered to prevent light with a wavelength less than 570 nm from being projected onto the slide.

The second light source 34 comprises a conventional light bulb with a filter to allow light with a wavelength of less than 540 nm to pass. The second light source 34 is also arranged to illuminate the portion of a patient 8 which is visible from the cameras 18, 20, 22. The filtration of the light from the second light source 34 prevents the light from the second light source 34, interfering and saturating the speckle pattern generated by the first light source 32.

In use, images of the speckle pattern are obtained by the geometry cameras 18, 22 as these cameras are arranged to detect light having a frequency of greater than 570 nm. These images from the geometry cameras 18, 22 are then subsequently processed so that the position and orientation of the surface of the body of the patient 8 visible from the geometry cameras 18, 22 can be determined and a three dimensional model of the surface of the individual generated as is described in WO 2004/004828.

In order to avoid saturation occurring at the boundaries of the speckle patterns, in this embodiment the first light source 32 of each camera rig 1, 2, 3 comprises a flash light source such as an arrangement of LED's. When images are desired the flash light sources 32 of different camera rigs 1, 2, 3 are then activated at slightly different times. In this way interference between patterns at the boundary of images obtained from different camera rigs 1, 2, 3 is avoided.

When a textured rendered model of a patient is desired, the images of the patient are obtained from the texture camera 20. These images are then utilised to texture render the model created from the geometry camera 18, 22 images. As the texture camera 20 is arranged only to detect light having a wave length of less than 540 nm, this image does not contain the speckle pattern projected by the first light source 32 but rather corresponds to the visible images perceived by an operator within the treatment room.

Figure 3:
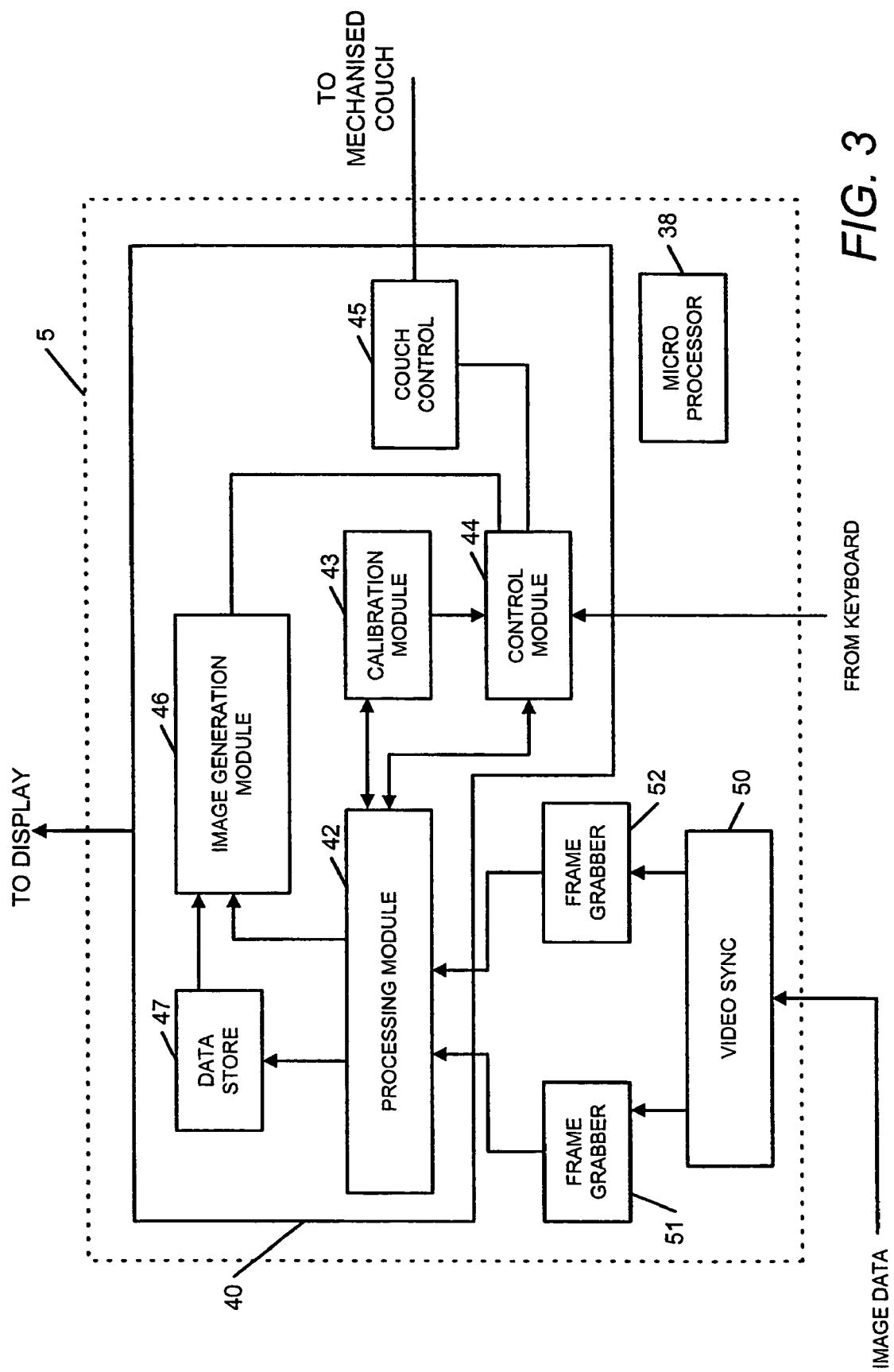
FIG. 3 is a block diagram of the computer of the patient positioning system of FIG. 1.

FIG. 3 is a schematic block diagram of the computer 5 of FIG. 1. The computer 5 comprises a microprocessor 38 and memory 40. The memory 40 is configured into a number of notional functional modules.

In this embodiment, these functional modules comprise a processing module 42 for controlling the microprocessor 38 to co-ordinate receiving and processing images; a control module 44 arranged to control the microprocessor 38 to receive signals from the keyboard of the computer 5 and co-ordinate the processing by the processing of the other modules; a calibration module 43 enabling microprocessor 38 to calibrate the positioning system so that relative to the point of focus of the treatment apparatus 6, the processing module 42 is able to identify the location of the surface of a patient 8; a mechanical couch control module 45 arranged to enable the microprocessor 38 to utilise generated surface models of an individual to generate positioning instructions which are then passed to the mechanical couch 7 of the treatment apparatus 6 so that a patient 8 may be automatically correctly positioned for treatment; an image generation module 46 to enable the microprocessor 38 to generate an image of the portion of the patient being treated and display it on the screen 11 of the computer 5; and a data store 47.

Also provided as part of the computer 5 are a video sync unit 50 and a first and a second frame grabber 51, 52. The first and second frame grabbers 51, 52 are arranged to receive image data from the three cameras attached to each of the camera rigs 1, 2, 3, specifically the first and second frame grabbers 51, 52 are arranged to receive video signals from the geometry cameras 18, 22 of the camera rigs 1, 2, 3 via the video sync 50. Video images for the six geometry cameras (two cameras on each of the three camera rigs) are received by the video sync 50 and passed to the two frame grabbers 51, 52, three to the first frame grabber 51 and three to the second frame grabber 52. The video sync 50 passes timing signals from the first frame grabber 51 to the second frame grabber 52 to ensure that image data from the geometry cameras 18, 22 is acquired simultaneously. By providing two frame grabbers 51, 52, in this way the computer 5 is arranged to receive image data from the geometry cameras 18, 22 of all three rigs 1, 2, 3 simultaneously so that an instantaneous three dimensional model of the surface of a patient 8 can be generated.

Use of the System

Figure 4:
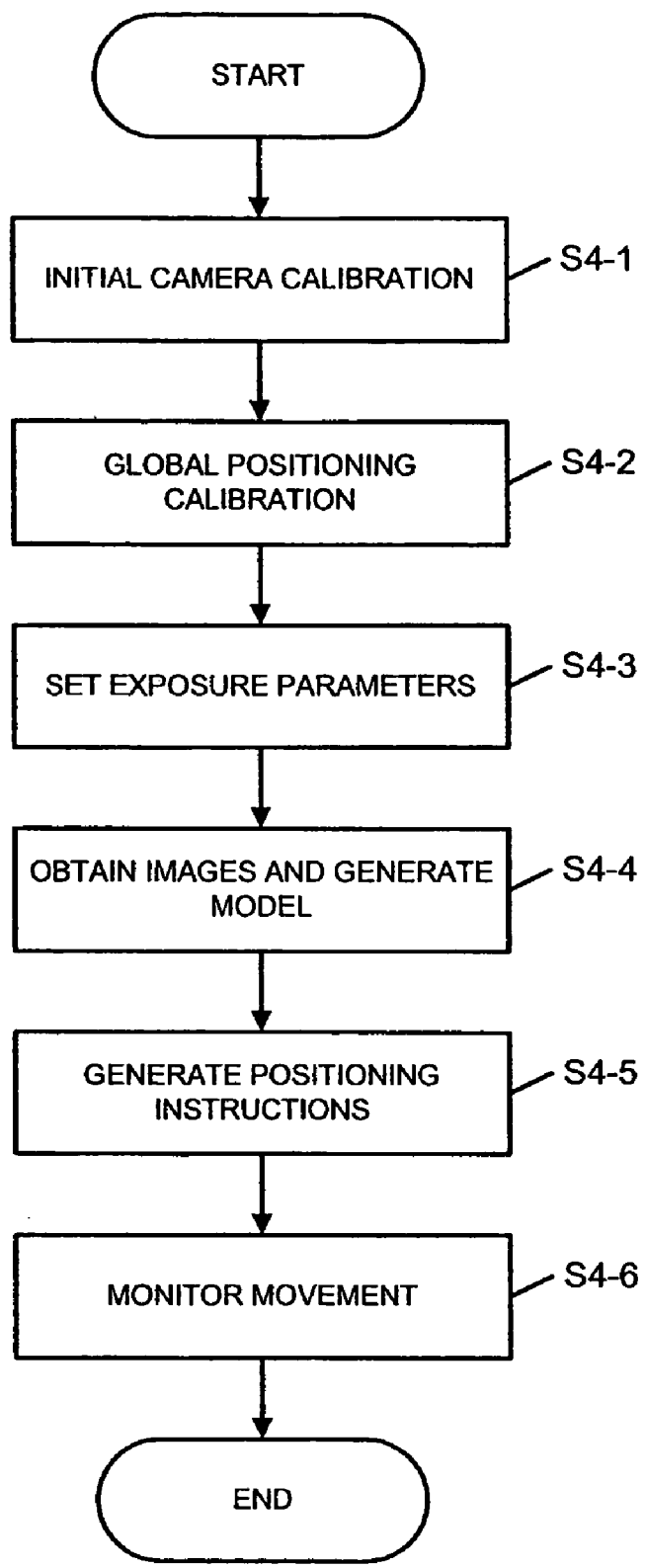
FIG. 4 is a an overview flow diagram of the use of the patient positioning system of FIG. 1.

An overview of the calibration and use of the patient positioning system will now be described with reference to FIG. 4 which is a flow diagram of the use of the system of FIG. 1.

Before any models of the surface of a patient 8 are calculated, the relative positions and orientations of the cameras 18, 20, 22 on each rig 1, 2, 3 relative to each other and also relative to the focussing point of the treatment apparatus 6 are calculated. This calibration of the cameras of the positioning system relative to the focussing point of the treatment apparatus 6 takes place in two steps. Initially, the system is calibrated so as to determine (S4-1) the relative positions and orientations of the cameras 18, 20, 22 on each of the rigs 1, 2, 3 relative to a fixed point. After this calibration has been achieved, the relative positionings of these cameras relative to the focussing point of the treatment apparatus 6 is then determined (S4-2).

The steps involved in the initial calibration (S4-1) for determining the relative positionings of the cameras 18, 20, 22 will now be described in detail.

Initial Camera Calibration

A calibration sheet comprising 70×70 cm sheet of flat rigid material such as aluminium or steel on which a pattern revealing a 34×32 matrix of circles at known positions on the surface of the sheet is provided. Additionally, towards the centre of the calibration sheet are four smaller markers adjacent to four circles the centres of which together identify the four corners of a square of known size and also a cross formed by a pair of dashed lines which meet at the centre of the sheet. When calibration is to occur, the sheet is held in position on the mechanical couch 7. Images of the calibration sheet are then obtained by all of the cameras 18, 20, 22 of a camera rig 1; 2; 3 being calibrated. These images are then processed to identify within the image the positions of the four markers in the images and their associated circles. This can be done either automatically using conventional techniques or alternatively, a user may identify the four circles manually.

From the relative positions of circles identified by the markers in the images, for each image a first projective transformation is determined which accounts for the estimated centres of the identified circles defining the corners of a projected distorted square in the image which arises due to the relative orientation of the calibration sheet and the camera obtaining the image. In this embodiment this first transformation determined is an estimated transformation for distorting the image so that the circle centres correspond to the corners of a square.

The calculated transform is then utilised to determine estimated 3 dimensional co-ordinates centres of each of the circles identified by markers. These calculated co-ordinates then identify an estimated location and orientation for the plane corresponding to the surface of the calibration sheet relative to the position from which an image has been obtained.

Each pixel in the image obtained by the camera 18;20;22 is then processed in turn to determine where within the plane containing the estimated positions of the circle centres, each pixel corresponds. The estimated circle centres are then processed in turn and the pixels in an image corresponding to points lying within a pre-determined distance from each circle centre in the calculated plane are then identified. In this embodiment, these areas are selected to encompass points lying within the plane of the calibration sheet up to a distance slightly larger than the radius of the circles appearing on the calibration sheet. Thus in this way for each circle a set of pixels is identified which correspond to the appearance of a portion of the sheet centred on the estimated centre position and extending slightly beyond the outer edge of the circle in question.

The grey scale values for each of the pixels in each set are then utilised determine an improved estimate of the co-ordinates for the circle centres. x and y co-ordinates for the positions of the points in the estimated plane including the surface of the calibration sheet each pixel represents with the set is determined. These calculated x and y co-ordinates are then utilised to estimate an improved estimates of the x,y co-ordinates of the circle centre using the following equations:

$$x = \frac{\Sigma gx}{\Sigma g} \quad y = \frac{\Sigma gy}{\Sigma g}$$

where $\Sigma g$ is the sum of all pixel values in the set identified for a particular circle centre, $\Sigma gx$ is the sum of the grey scale pixel values for a pixel multiplied by the x co-ordinates for those pixels and $\Sigma gy$ is the sum of the grey scale pixel values for a pixel multiplied by the y co-ordinates for those pixels, and where the colour of the circle is associated with a high grey scale value and the colour of the background corresponding to the calibration sheet is associate with a low grey scale value.

Co-ordinates for the point within the image corresponding to the new estimated circle centres are then determined from these x,y co-ordinates and these updated estimates of the centres of the marked circles are then utilised to determine a more accurate estimated transformation to account for the location and orientation of the calibration sheet. The above process can then be repeated until an accurate estimate of the actual circle centre positions is made and the true transform required to account for the relative orientation of the calibration sheet is determined.

Using the final determined transform, the expected positions of all of the circles on the sheet appearing in the image are then calculated, the portions of the images in the vicinity of each of the estimated circle centres are then processed individually in the same way as described above. For each of the circles a set of pixels is identified corresponding to points within a preset distance to the circle centre and then an improved circle centre co-ordinate is calculated using the grey scale values and co-ordinate values as described above.

When the co-ordinates for all the centres of each of the representations of the circles on the calibration sheet have been calculated for an image, the relative orientation of the different cameras 18, 20, 22 on one of the camera rigs 1, 2, 3 can then be calculated from the relative positions of these points in the images and the known relative locations of these circles on the surface of the calibration sheet as is described in detail in "A Versatile Camera Calibration Technique for High-Accuracy 3D Machine Vision Metrology Using Off the Shelf TV Cameras and Lenses", Roger Tsai, IEEE Journal of Robotics and Automation, Vol. Ra-3, No.4, August 1987. Further from the relative positions of the points in the individual images internal camera parameters such as the focal length and radial distortion within the camera images can also be determined. This information is then stored within the data store 47 of the memory 40 of the computer 5 for use in subsequent generation of accurate three dimensional representations of the surface of a patient.

When the camera positions and internal camera parameters have been determined for all of the cameras 18, 20, 22 for all three of the camera rigs 1, 2, 3, the positioning of the cameras relative to the focusing point of the treatment apparatus 6 is then determined (S4-2) as will now be explained.

Global Positioning Calibration

In this embodiment as has previously been described a laser projection system 9 is provided which is arranged to project three sets of laser beams 10 projecting planes of light collectively identifying the focusing point of the treatment apparatus 6. This focusing point is also known as the iso-centre for the treatment apparatus 6. In a conventional manner the calibration of this laser equipment 9 and the treatment apparatus 6 is such that a user is able to use the projection of the laser beams 10 to identify the iso-centre of the treatment apparatus 6 when treatment is occurring.

Additionally, in a conventional treatment apparatus 6, a cross hair target is provided at the centre of the radiation beam generated by the treatment apparatus 6. Light projected from behind this target then causes a shadow of the target to be projected thereby identifying the centre of a radiation beam generated by the apparatus. The laser beams 10 and the shadow projected from the treatment apparatus 6 are utilised to help the relative positions of the cameras of the camera rigs 1, 2, 3 to be determined relative to the iso-centre as will now be described with reference to FIG. 5.

Figure 5:
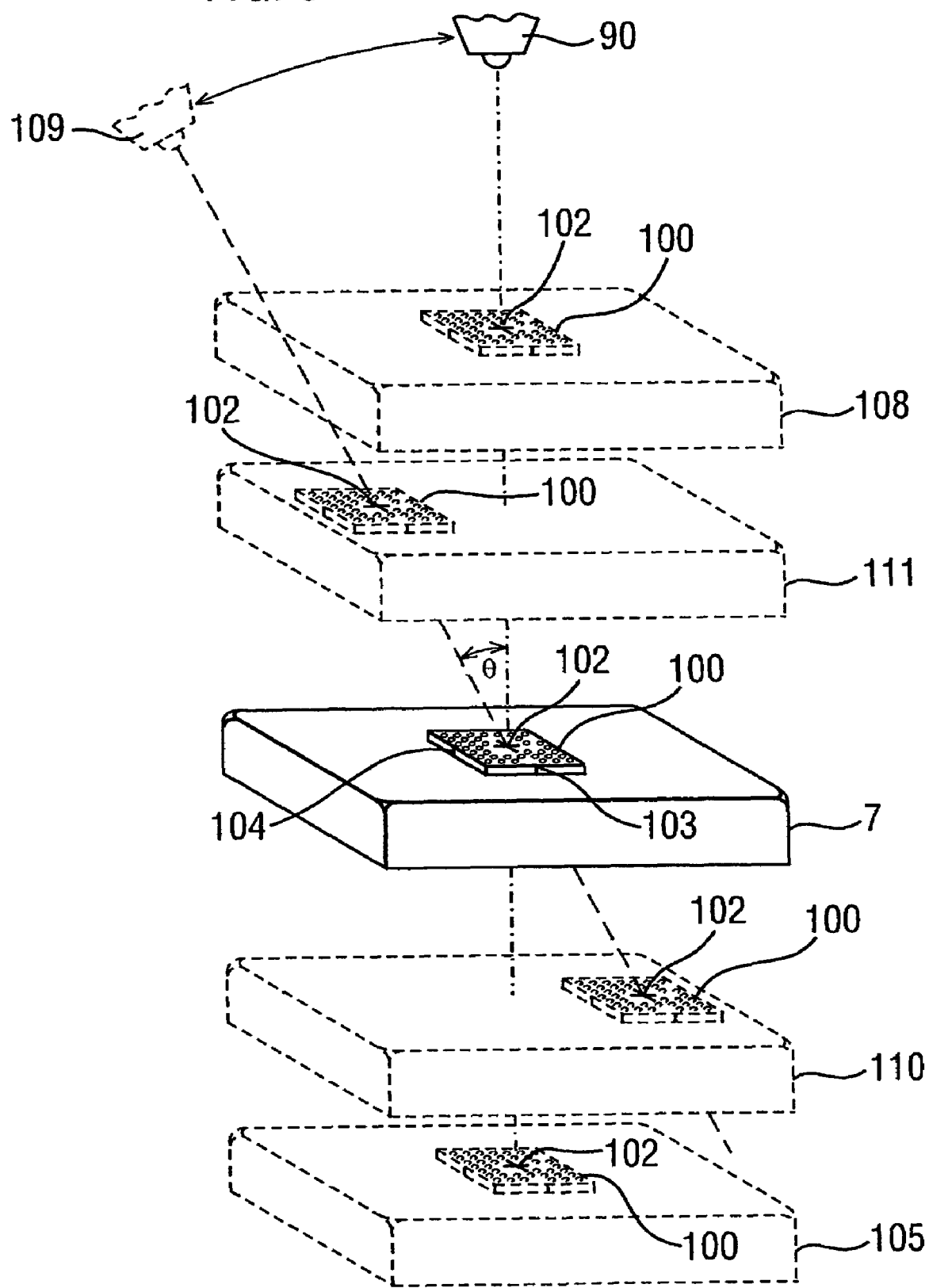
FIG. 5 is a schematic illustration of the use of a calibration sheet to calibrate the positioning system of FIG. 1.

In this embodiment when calibrating the patient positioning system relative to the iso-centre for the treatment apparatus 6 the same calibration sheet is used as is described in relation to the camera calibration. FIG. 5 illustrates the gantry 90 of the treatment apparatus 6 and the surface of patient positioning couch 7 on which the calibration sheet 100 is placed. As described, this calibration sheet 100 in addition to the circles previously described also has a target formed by dashed lines defining a cross 102 at the centre of the sheet. Down the edges of each of the sheet lines comprising extensions of the dashed lines are also marked 103,104.

Initially the patient positioning couch 7 is adjusted so that the laser light from the light projectors 9 just skims over the surface of the calibration sheet 100. The marks 103,104 on the edge of the calibration sheet 100 are then aligned with the projected planes of laser light so that, as far as possible, the cross centre 102 is located at the iso-centre as defined by the intersection of the planes of light projected by the laser light projectors 9.

At this point, with the gantry 90 an initial zero position, the shadow of cross hair target in the gantry 90 formed by light projected from the gantry 90 should coincide with the centre of cross 102 on the calibration sheet 100. That the cross 102 is located at a position very close to the iso-centre of the treatment system can then be checked by rotating the gantry 90 through an angle θ of say for example 45°. As the gantry rotates if the centre of the cross 102 is located at the iso-centre the projected shadow of the cross hair target from the gantry 90 will not appear to move. If noticeable movement can be detected when the gantry 90 is rotated, the position of the calibration sheet 100 is adjusted until this is no longer the case.

Once the calibration sheet 100 has been placed as far as possible with the cross 102 located at the iso-centre, the position of the mechanical couch 7 is then adjusted so as to reduce the height of the couch 7 and place the calibration sheet 100 in a new position 105 beneath the identified iso-centre. To ensure that the calibration sheet remains within the clear view of the camera rigs 1, 2, 3, in this embodiment, this new position 105 is selected to be approximately 20 cm beneath the iso-centre. From the initial positioning, the shadow of the cross hair target in the gantry should if the couch is accurately calibrated still be coincident with the target 102 on the calibration sheet 100. If this is not the case the position of the sheet 102 is further adjusted so that this is the case. Images of the calibration sheet 100 in this position 105 are then captured by the cameras of the camera rigs 1, 2, 3 and utilizing the captured images the location of the centre of the cross 102 on the calibration sheet is determined by the calibration module 43.

In order to maximize the accuracy with which the location of the cross 102 is determined in this embodiment the images obtained by the cameras of the camera rigs are processed to calculate three dimensional co-ordinates for the centres of all of the circles on the calibration sheet 100. Using the conventional Procrustes algorithm an estimated transform necessary to fit a stored model of the calibration sheet 100 with circle centres at predefined locations is determined. In this way by utilizing measurements for all the estimated locations of visible circle centres, any errors in the calculated positions can be corrected for through the fitting of model sheet to the estimated positions. The location of the centre of the cross 102 on the calibration sheet 100 is then determined through the application of the calculated transformation to the origin of the cameras' co-ordinate frame.

It will be appreciated that in alternative embodiments the location of the cross 102 could be calculated by processing the obtained images to identify the position of the cross itself. Such an alternative approach would however only be as accurate as the estimate of the location of the cross centre in the images. For this reason determining the 3D co-ordinates for the cross centre through calculating multiple estimates of circle centre positions and extrapolating an estimated position for the cross centre is preferred.

The position of the mechanical couch 7 is then adjusted by raising the couch 7 by approximately 40 cm so that it lies roughly 20 cm above the position of the determined iso-centre. The positioning of the calibration sheet is then confirmed using the target cross hairs and adjusted if necessary before the camera rigs 1, 2, 3 are utilized to capture images of the calibration sheet 100 in this second position 108. Images of the calibration sheet 100 in this new position are then processed by the calibration module 43 as described above to identify the location of the cross 102 in these new images.

Thus in this way the camera system is able to obtain images of the calibration sheet 100 where the cross 102 is located at two points along the path of the light projected from the gantry 90 in its zero position After images of the calibration sheet 100 in the second position 108 have been captured, the couch is again adjusted so that the surface of the couch 7 lies beneath the estimated position of the iso-centre. As previously discussed normally in this embodiment, this distance is selected to approximately 20 cm beneath the estimated iso-centre position. The gantry 90 is then rotated to a new position 109 a preset angle θ from its original zero position. A suitable rotation would be with the preset angle θ being 45°. The position of the calibration sheet 100 is then adjusted so that the cross projected from the gantry 90 again coincides with the cross 102 appearing on the calibration sheet 100 in its new position 110. Once the calibration sheet 100 has been located in position, the gantry is returned to its zero position 90 to ensure the gantry does not obscure any of the camera views and images of the calibration sheet 100 in its new position 110 are obtained and processed by the calibration module 43 to identify the current location of the cross 102 in this new position 110.

This procedure is then repeated with the mechanical couch 90 a selected distance above the estimated iso-centre position of about 20 cm with the calibration sheet 100 being repositioned once more so that the cross 102 on the surface of the calibration sheet 100 coincides with the light projected from the gantry when the gantry is at the selected predetermined angle θ from its origin location. Images of the calibration sheet 100 in this final position 111 are then obtained and processed.

Thus in this way the camera system is able to obtain images of the calibration sheet 100 where the cross 102 is located at two points along the path of the light projected from the gantry 90 when it is rotated at an angle of θ degrees relative to its start position. Since the treatment apparatus 6 will be set up so that the rotation of the gantry 90 does not vary the location of the focus of the treatment system 6, the iso-centre can then be established by determining the intersection of the line joining the identified positions of the crosses 102 in the obtained first and second pairs of images.

Data identifying calculated location of the iso-centre is then stored by the calibration module 40 together with data defining the transformations necessary to translate data generated in the co-ordinate system for the camera rigs 1, 2, 3 to a co-ordinate system relative to this identified iso-centre position where the z axis of the new co-ordinates is orientated along the axis which corresponds to the movement of the calibration sheet 100 between the first two images and the y z plane contains all four points identified as cross centres in all four images.

Thus utilizing this stored data, the patient positioning system is then able to generate models of a patient's surface where points on the surface are identified in a common co-ordinate system defined as being relative to the identified iso-centre.

Returning to FIG. 4, after the patient positioning system has been calibrated, and it is desired to generate a computer model of a patient 8 lying on the couch 7, as a first step exposure values for the geometry cameras 18, 22 of the camera rigs 1, 2, 3 are calculated (S4-3) as will now be described with reference to FIG. 6.

Determination of Required Exposures

The applicants have determined that in order to maximize the quality of models generated by the system, it is important that the geometry cameras 18, 22 of the camera rigs 1,2,3 have exposures selected so that the projected speckle pattern projected onto a patient 8 is easily identified. Further, it has been determined that optimal exposure settings vary from patient to patient due to differences in skin colour and differences in skin reflectance dependent on how hairy a patient is and also arising due to oily or sweaty skin. Therefore in order to optimize the quality of images obtained by the cameras, in this embodiment exposure parameters of the geometry cameras 18, 22 are varied from patient to patient.

Figure 6:
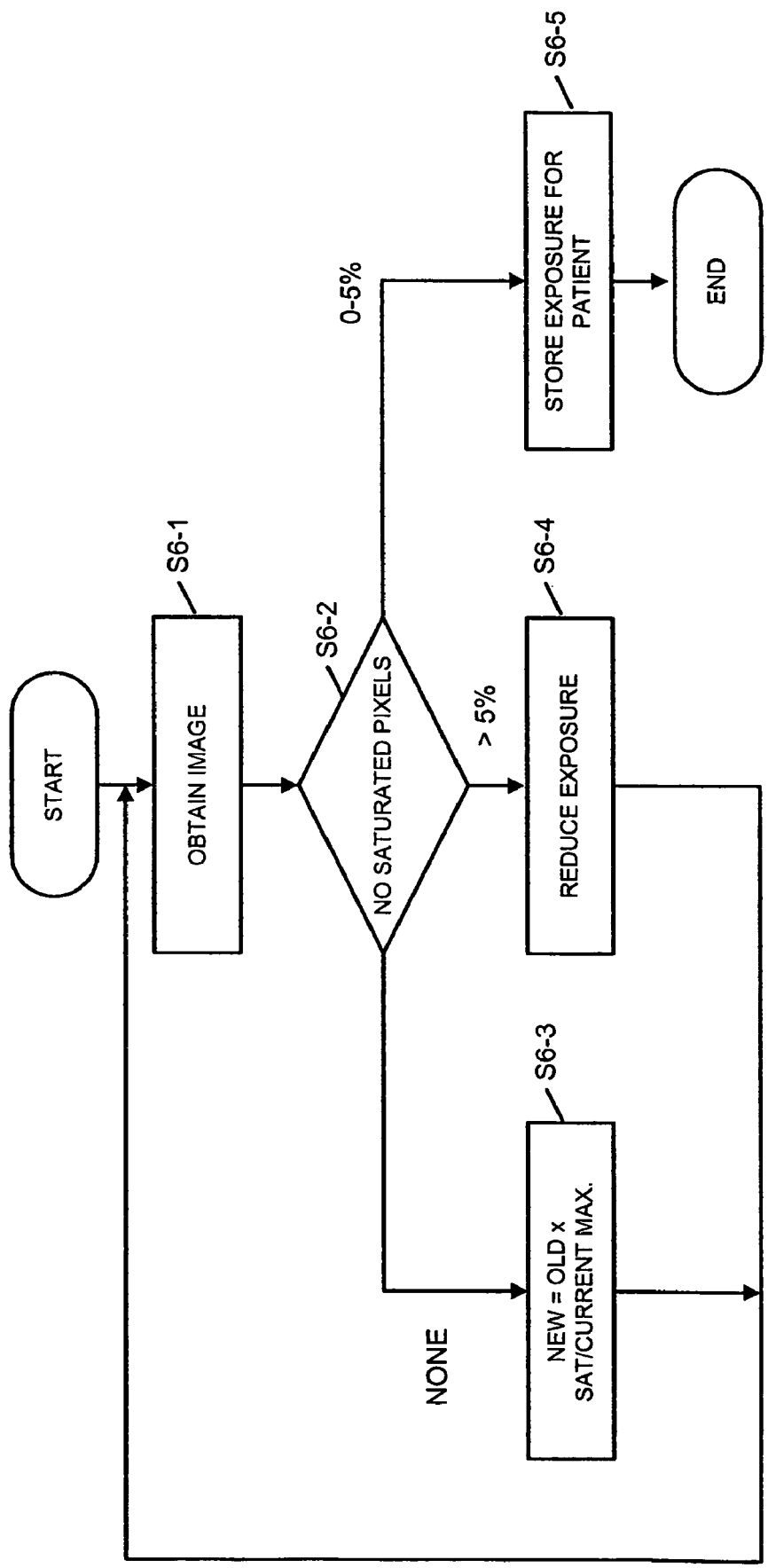
FIG. 6 is a flow diagram of the processing of the computer of the patient positioning system of FIG. 1 for setting exposure levels.

Referring to FIG. 6 which is a flow diagram for the processing performed to select appropriate exposure parameters, for each geometry camera 18, 22 initially an image of a patient 8 onto which the speckle patterns is projected is obtained (S6-1).

The processing module 42 then (S6-2) proceeds to count the number of saturated pixels appearing in the obtained image. That is to say the processing module 42 identifies the number of pixels in an obtained image has a value of 255.

If it is determined that none of the current pixels in the image has a value of 255, a longer exposure is calculated (S6-3) by multiplying the previous exposure time by a saturation intensity value (SAT) divided by the greatest of the pixel values of the obtained image where the saturation intensity value (SAT) is a pre-stored parameter dependent upon the cameras being used. The processing module 42 then causes a further image (S6-1) to be taken utilizing the revised exposure time and checks once again (S6-2) the number of saturated pixels included in the image.

If when counting the number of saturated pixels in an image (S6-2) the processing module 42 determines that the number of saturated pixels exceeds a preset proportion of the number of pixels which in this embodiment is set to 5%, the processing module 42 then automatically reduces the exposure time to a low value so as to eliminate saturated pixels so that when a new image is obtained (S6-1) no saturated pixels will be present and the exposure time can be iteratively adjusted using the pre-stored saturation intensity variable (S6-3).

When an image is obtained by the camera (S6-1) and the processing module 42 establishes (S6-2) that some but less than the threshold number of pixels appear saturated, this exposure value is stored (S6-5) for that particular patient and camera and utilized to obtain images for generating a model of the surface of that patient.

Returning to FIG. 4 once exposure parameters have been set for a particular patient, the computer 5 then (S4-4) instructs the camera of the camera rigs 1, 2, 3 to obtain images of the patient onto which a speckled pattern is projected by the speckle projector 32. These images are then processed in the manner described in WO 2004/004828 so as to generate a computer wire mesh model of the patient based on the known relative positions of the different cameras in the camera rigs 1, 2, 3 and the differences in the apparent shape and positions of the speckle pattern in the images obtained by different cameras on the same camera rig 1, 2, 3.

When a wire mesh model of the surface of a patient has been generated, the computer 5 then generates (S4-5) positioning instructions to cause the mechanical couch 7 to be positioned so as to match as closely as possible the surface of the patient 8 as represented by the generated wire mesh model with a pre-stored representation of the same patient positioned during the planning phase of the treatment.

Generation of Positioning Instructions

Figure 7:
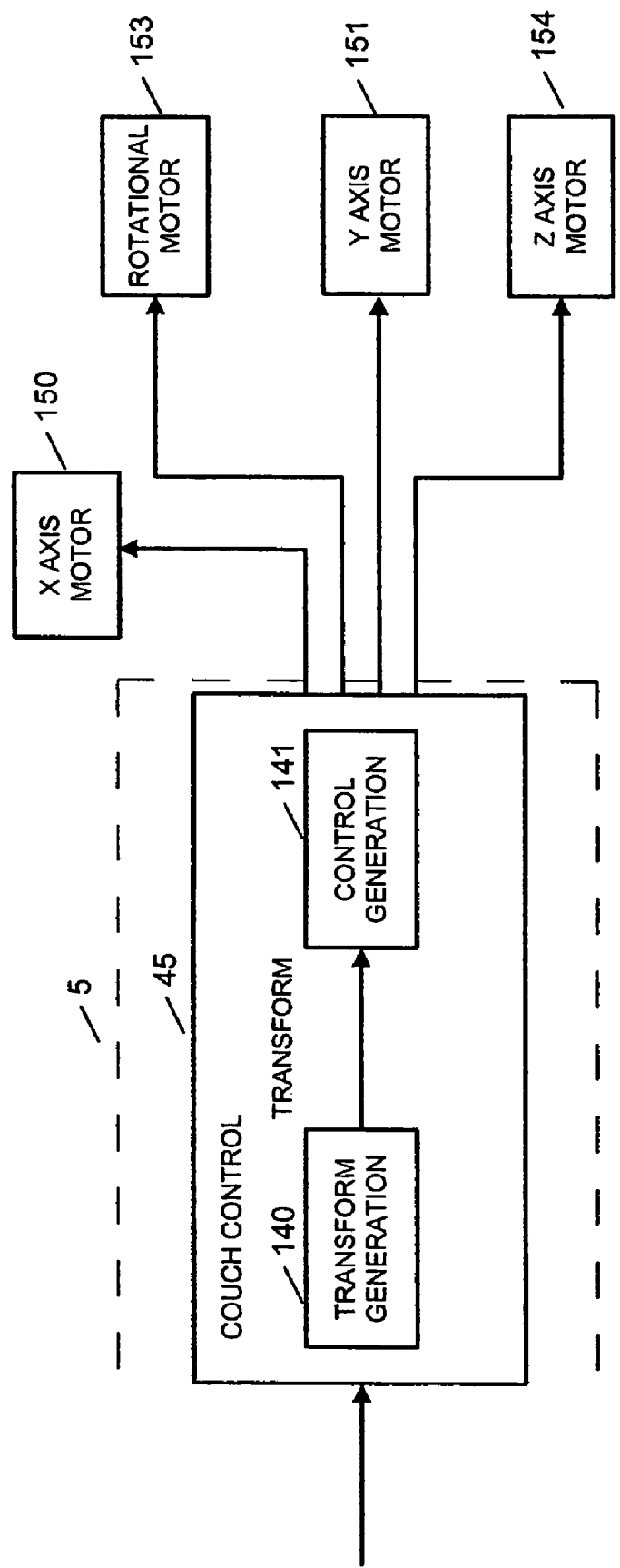
FIG. 7 is a schematic illustration of the control system for varying the position of the mechanical couch of the patient positioning system of FIG. 1.

FIG. 7 is a block diagram of the control system for positioning a patient. In this embodiment, the couch control module 45 comprises a transform generator 140 for calculating a transform for matching a generated model surface with a stored surface and a control generation module 141 for generating control signals for controlling an x axis motor 150, a y axis motor 151, a z axis motor 152 and a rotational motor 153 respectively arranged to move the mechanical couch 7 laterally, longitudinally, vertically and rotationally relative to the iso-centre of the treatment room.

Figure 8:
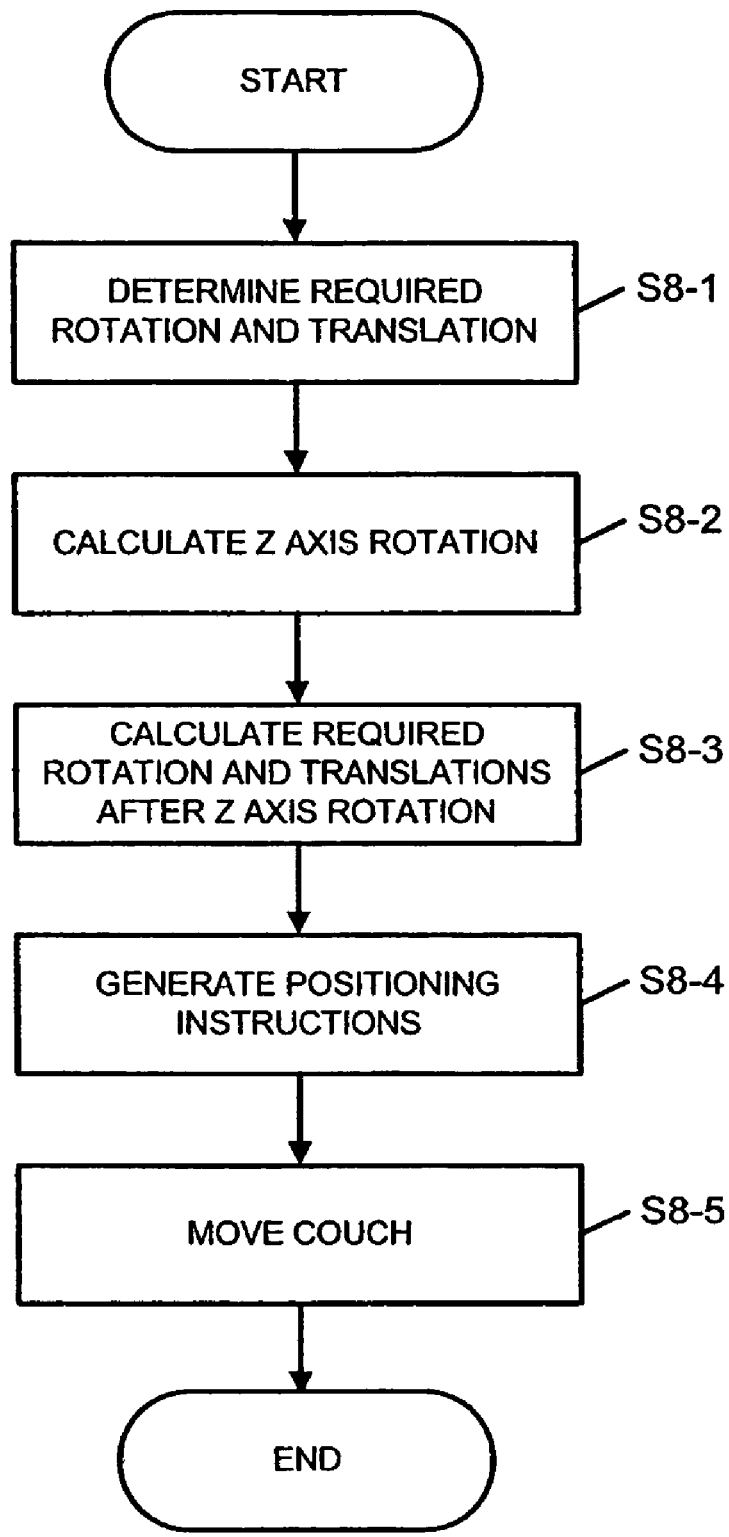
FIG. 8 is a flow diagram of the processing of the computer of the patient positioning system of FIG. 1 to calculate movement instructions.

FIG. 8 is a flow diagram of the processing performed by the couch control module 45.

Initially, (S8-1) the transform generation module 140 of the couch control module 45 determines a first required transform for aligning the generated model of the patient surface and corresponding stored model of the patient.

As is described in greater detail in WO 2204/004828, this determination of the first required transform is a two stage process. Initially the transform generation module 140 determines a rough transformation for aligning the newly generated surface model with a pre-stored model surface by generating a decimated representations of the two models and identifying the closest matching points using conventional Procrustes algorithm techniques such as are described in "Least Square Fitting of Two 3D Point Sets" Arun et al, IEEE Transactions on Pattern Analysis and Machine Intelligence Vol PAMI-9 No. 5 pp698-700, 1987, and "Closed Form Solution of Absolute Orientation Using Unit Quaternions' B. K. P. Horn J. Opt-Soc. Am. A. Vol 4, No. 4, pp629-642, April 1987 both of which are hereby incorporated by reference.

The process then iterates utilizing the iterated closest point (ICP) algorithm as is described in "A Method for Registration of 3-D Shapes" Paul J. Besl and Neil D McKay, IEEE Transactions on Pattern Analysis and Machine Intelligence, Vol 14, No. 2 February 19 7 pp239-256, which is also hereby incorporated by reference.

After an initial rough transformation has been determined, the rough transformation is then refined by determining, for all vertices of the generated model to which the initial transformation has been applied, the closest points on the surface in the pre-stored model as is described in WO 2004/004828. When the closest points on the surface defined by the pre-stored model to the vertices of the generated model have been identified, the ICP algorithm is repeated to determine a final matching transformation.

The final matching transform determined by the transform generation module 140 after refining the initial rough transform will comprise a 6-degree of freedom transformation:

$$S = \begin{pmatrix} R & T \\ 0 & 1 \end{pmatrix}$$

where R is a 3×3 rotation matrix representing a general rotation which can be considered to consist of an initial rotation about the z axis $R_z$ followed by a rotation about the y axis $R_y$, followed by a rotation about the x axis $R_x$, T is a 3×1 translation vector and S is a 4×4 transformation matrix, so that where a point x is translated to a point x', x'=$R_x R_y R_z$ x+T where R=$R_x R_y R_x$ and T is the linear translation vector described above.

The surface of a mechanical couch 7 is flat and is not arranged to tilt from this flat position. When a transformation is calculated using the ICP algorithm, although theoretically, a transform matching the surface of a patient on any two occasions should give rise to a transformation which can be effected by the mechanical couch, in practice due to rounding errors and the fact that a patient is not a perfectly rigid body errors arise which frequently result in part of a calculated transform S including a calculated rotation matrix R where R≠$R_z$ i.e. $R_x$ and $R_y$≠0. Positioning a patient using the calculated translation T and only the calculated rotation about the z axis $R_z$ ignoring the other rotational elements $R_x$ $R_y$ can lead to significant errors because the subsequent translation T proceeds to exaggerate the difference between using R and only the rotation about the z axis $R_z$.

The applicants have determined that a more accurate positioning of the patient is achieved by extracting the z axis rotation $R_z$ from this initial calculated rotation R and then recalculating a new translation vector $T_z=T_z(x)+T_z(y)+T_z(z)$ where $T_z(x)$, $T_z(y)$ and $T_z(z)$ are linear translations along the x, y and z axes respectively so that as far as possible the differences in positions which are determined to represent rotation about the other two axes can be accounted for by translational movement rather than a rotation which the couch is unable to perform.

Thus once the initial transform has been calculated (S8-1), the transform generation module 140 then proceeds (S8-2) to extract the rotational element about the z axis $R_z$ from the initial transform.

After this calculated rotation $R_z$ about the z axis has been extracted, a new translation vector $T_z$ is determined. This new transformation vector $T_z$ is derived from the original transformation vector T, the original calculated rotation element R of the calculated transform S and a determined value for the centroid of the surface of the model $x_c$ using the following equation:

$$T_z=(Rx_c+T)-R_zx_c$$

The transform generation module 40 then passes to the control generation module 141 a constrained transformation matrix $S_z$ $$S_z = \begin{pmatrix} R_z & T_z \\ 0 & 1 \end{pmatrix}$$

so that a point x will become transformed to a point $R_zx+T_z$. The control generation module 141 then (S8-4) generates signals which are passed to the x axis motor 150, the y axis motor 151, the z axis motor 152 and the rotational motor 153 to effect movement of the couch in the x, y and z axis and a rotation about the z axis where the movement in the x axis comprises a movement corresponding to $T_z(x)$ movement in the y axis comprises a movement corresponding to $T_z(y)$ and movement in the z axis comprises a movement corresponding to $T_z(z)$ and the rotation about the z axis comprises the calculated rotation about the z axis $R_z$.

As a result of the transfer instructions from the control generation module 141 to the motors 150-153, the motors are then activated and the surface of the mechanical couch is then moved (S8-5) which brings the surface of the patient so as to as closely as possible match the surface represented by the stored model of that patient.

As will be described in detail later, it is possible to utilize the models generated by the present invention to monitor a patients breathing cycle. In order to position a patient as accurately as possible, it is desirable to minimize variations in positioning instructions which arise due to reference surfaces being generated for different points within a breathing cycle. It has been determined that usually the most stable point in the breathing cycle for capturing and utilizing reference surfaces is when a patient has just expired and before the patient begins to inhale once again. Thus to maximize the accuracy with which a patient is positioned a reference model of the surface of a patient during planning is obtained at this point in the breathing cycle and similarly a new wire mesh model of the patient in their current position at this point in the breathing cycle is also obtained and matched.

Returning to FIG. 4, after a patient has been positioned based on the generated surface model and a stored surface model for that patient, the camera rigs 1, 2, 3 and computer 5 then proceed to monitor the patient (S4-6) whilst treatment is performed.

Patient Monitoring

As is described in detail in WO 2004/004828 using the techniques described in that application, after a patient has been positioned, the camera rigs 1, 2, 3 and computer 5 can generate models of the surface of a patient 8 during treatment and update those models very rapidly so as to monitor how a patient moves during treatment for example due to the patient's breathing cycle. In the earlier application, the monitoring of a patient is described in terms of visual representations of the manner in which the surface moves and differs from a pre-stored reference surface which is displayed on the screen 11 of the computer 5. The applicants have appreciated that further measurements of a patient's position and movement and breathing can also be derived utilizing the generated model surfaces as will now be described in detail with reference to FIGS. 9-12.

Figure 9:
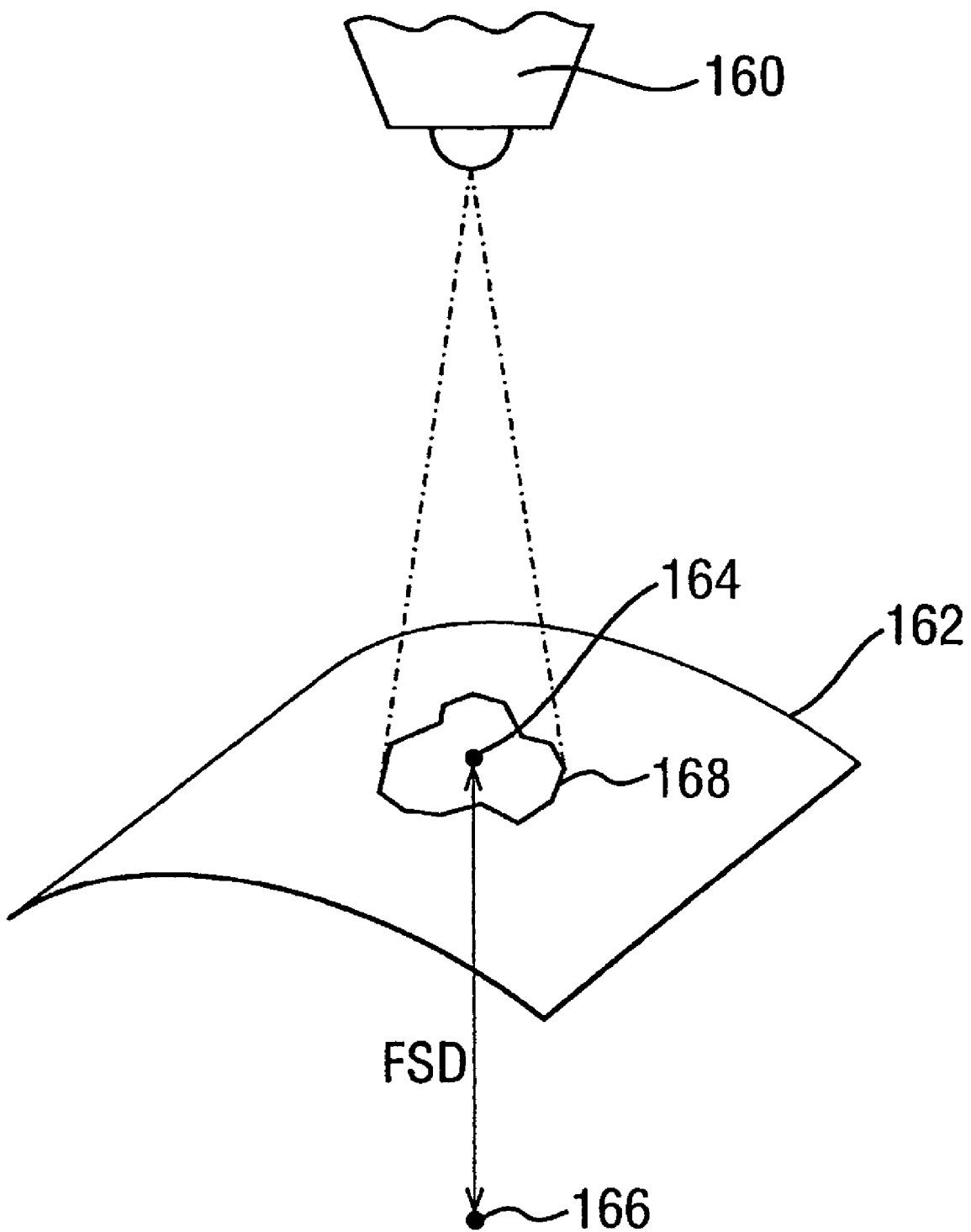
FIG. 9 is a schematic diagram illustrating the focus to skin distance of a radiation beam and the area of an individual irradiated by that beam.

FIG. 9 is a schematic illustration of the gantry 160 of a treatment apparatus irradiating the surface 162 of a patient 8. One measurement which is frequently used in radiotherapy is the focus to skin distance or FSD. This is the distance between the point 164 where of the centre of a generated radiation beam impinges on the surface 162 of patient and the focus position of the radiation beam 165 generated by the apparatus 6. Conventionally, this origin position 165 is a fixed distance from the iso-centre 166 of the treatment apparatus 6 for example 1 metre from the iso-centre 166. Additionally, information on the extent 168 of the surface 162 of a patient 8 which is actually irradiated by a radiation beam is useful to establish which areas of a patient have been irradiated so that those areas can be avoided in subsequent treatments.

It is therefore desirable to be able to process the wire mesh models generated by the computer 5 to establish both where a ray from the centre of a radiation beam impinges on the surface of a patient so that the FSD can be calculated and it is desirable to be able to identify points on the surface 168 to which the outer edge of the radiation beam extends to.

The applicants have appreciated that both of these measurements can be achieved by identifying for particular defined ray paths where a particular ray intersects with the model's surface. In the case of a ray modelling the centre of the beam, this will impinge at a particular point 164 and once this point is known, the FSD can be calculated. Similarly, in order to identify the extent of the surface 168 which is irradiated by a beam, a number of rays can be modelled based on data defining the shape of the beam generated by the treatment apparatus 6 and the extent to which that beam shape diverges. After the points on the surface where these rays intersect the model have been established the extent of the beam as it impinges on the surface can be identified.

Figure 10:
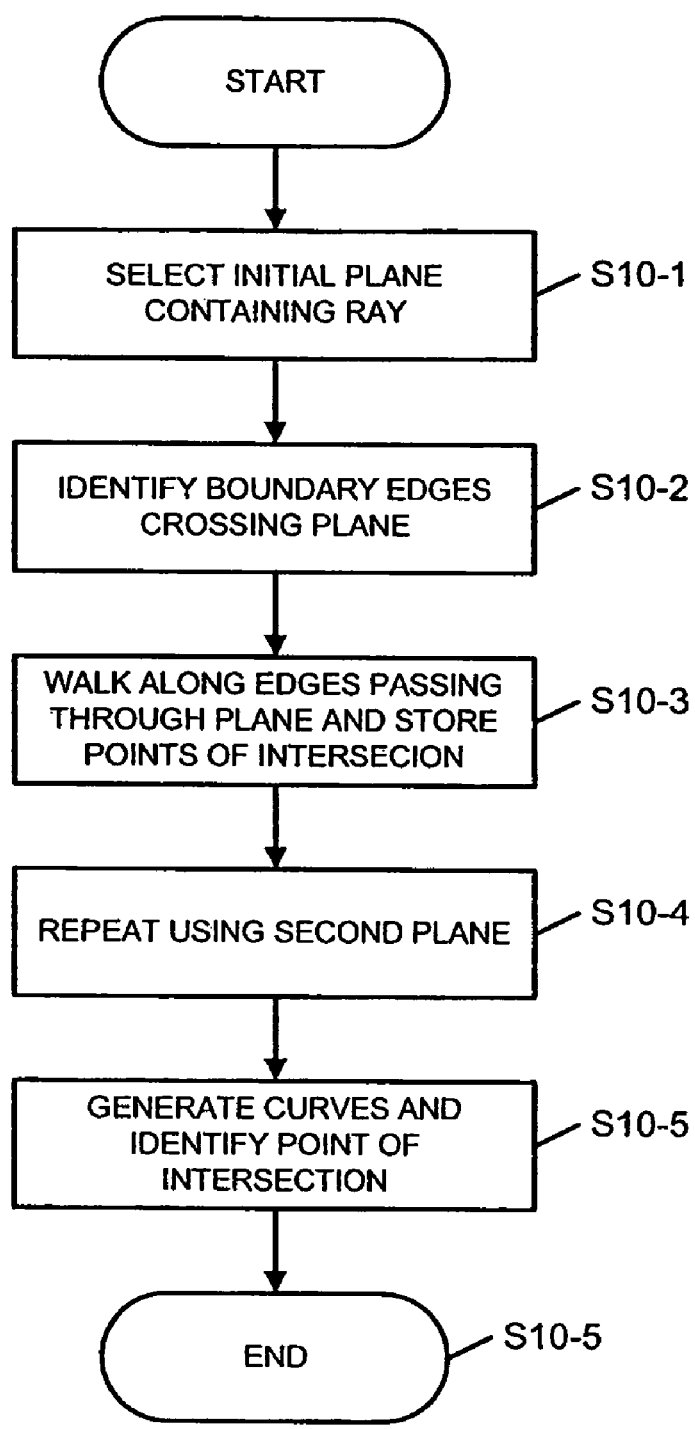
FIG. 10 is a flow diagram of the processing of the computer of FIG. 1 to calculate the point of intersection of a ray with a generated model surface of a patient.
Figure 11:
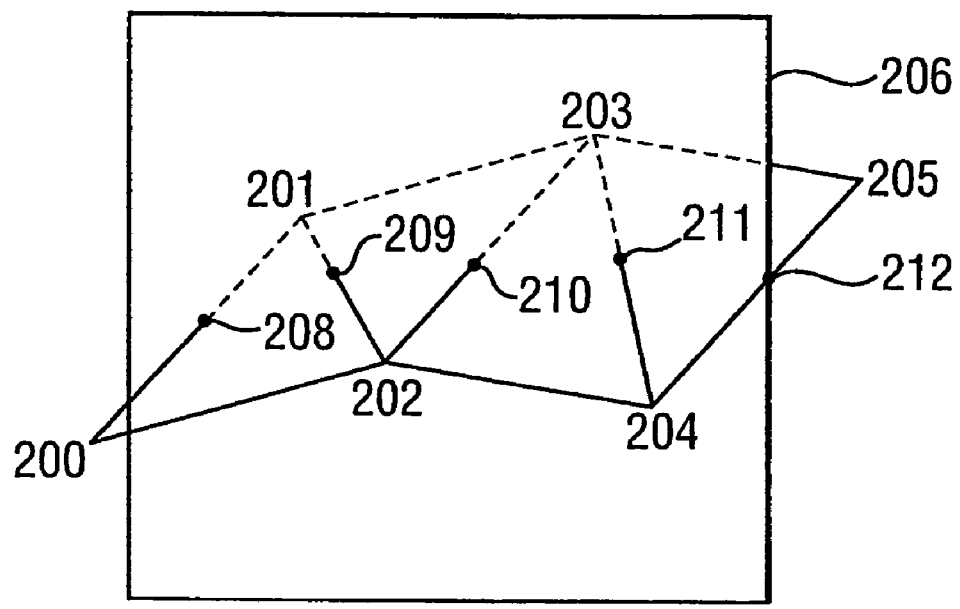
FIGS. 11 and 12 are schematic illustrations for explaining some of the steps of the flow diagram of FIG. 10.
Figure 12:
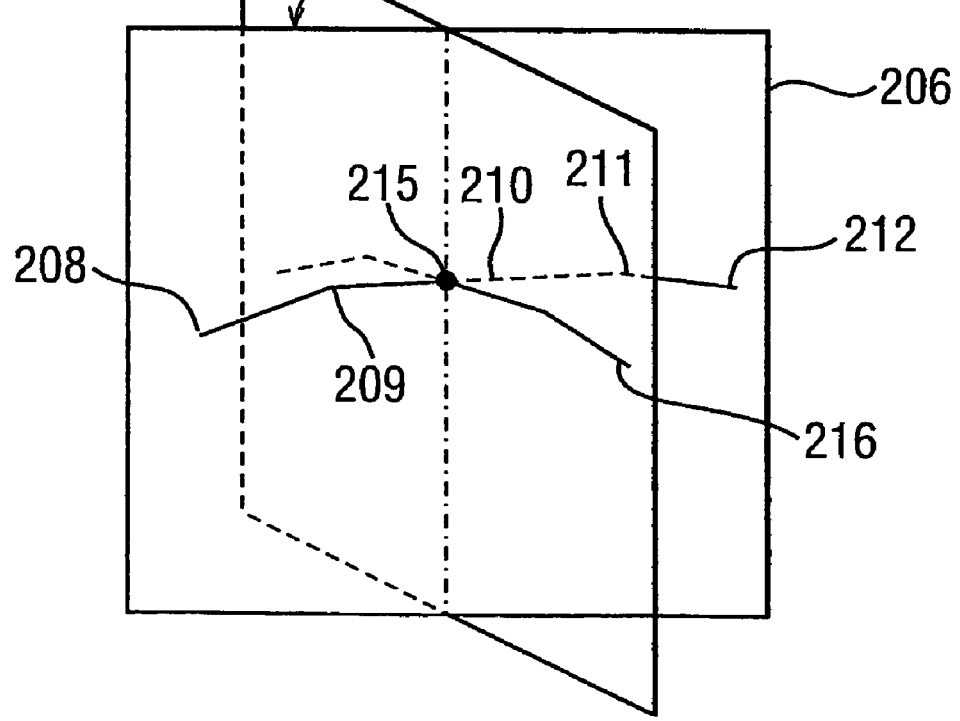

FIGS. 10-12 illustrate a technique for processing a wire mesh model to identify where a vector of known origin and direction representing a ray impinges on the surface of a wire mesh model.

Referring to FIG. 10, which is a flow diagram of the processing performed by the computer 5 to identify the point of intersection, initially (S10-1) the computer 5 selects a plane which contains the ray being modelled. In this embodiment, in the case of a ray at the centre of a radiation beam, this initial plane is selected as the plane defined by the z and y axis of the treatment and mechanical couch 7.

The computer 5 then identifies the boundary edges of the wire mesh model which intersect this plane. In order to identify boundary edges in the wire mesh model which intersect the plane, in this embodiment once a wire mesh model of the surface has been generated, data is stored identifying all the pairs of vertices connected by edges at the boundary of the surface generated by the computer 5. Each of these boundary edges is then processed in turn. The calculated signed projected distance of each vertex to the plane is then calculated. This value is equal to $(p-x) \cdot n$ where $p$ is a point on the plane for which intersection is being determined $n$ is a unit vector normal to that plane and $x$ is the co-ordinate of the vertex being processed.

Whenever a pair of vertices corresponding to a boundary edge of a generated model are identified where the sign of the calculated signed projected distance for one of the vertices connected by the edge is positive but negative for the other, this indicates that the two vertices lie either side of the plane defined by p and n and data identifying the pair of vertices is stored.

Once all of the boundary edges of the generated surface which are bisected by the selected plane have been identified (S10-2) the points of intersection of these boundary edges with the plane 206 and the other edges in the wire mesh model bisected by the selected plane are then identified (S10-3).

The manner in which this is achieved is illustrated by FIG. 11 which is schematic diagram of a portion of a wire mesh surface connecting a set of vertices 200-205 bisected by a plane 206.

After having tested all of the boundary edges for the generated surface, the computer 5 will have stored data identifying all the bisected boundary edges. In the case of the example of FIG. 11 this will establish the boundary edges linking vertex 200 and 201 and vertex 204 and 205 are bisected by the plane 206 which is being processed. A first of these boundary edges is 200-201 is selected and the point of intersection of this edge with the plane being processed is determined in a conventional manner. Data identifying the point of intersection 208 of this edge with the plane 206 is then stored.

The computer 5 then identifies the other vertex 202 which is connected into both of the vertices of the edge 200-201 which has just been processed. The computer then establishes whether signed projected distance the newly identified vertex 202 to the plane 206 being processed either shares the same sign with the signed projected distance to the plane 206 with the first 200 or second 201 vertex of the selected boundary edge 200-201. The edge 201-202 connecting the vertices 201,202 associated with different signs of signed projected distance is then selected as the next edge to be processed and the intersection 209 of that edge 201-202 with the plane 206 is then calculated in a conventional manner and then stored.

The computer 5 then checks whether the newly selected edge 201-202 is also one of the edges intersecting the plane 206 which was previously identified as being a boundary edge of the surface. If this is not the case, the other vertex 203 of the triangle including the newly identified edge 201-202 is identified. In the same way as has previously been described, the signed projected distance to the plane 206 for this newly identified vertex 203 is determined and the computer 5 establishes which of the other vertices 201,202 of this new triangle is associated with a signed projected distance of the opposite sign. The edge 202-203 connecting the new vertex 203 with a vertex 202 associated with a signed projected distance of the opposite sign is selected and the point of intersection 210 of this edge 202-203 with the plane 206 is determined and stored before the computer 5 checks once again whether the edge 202-203 has previously been identified as a boundary edge and if not the edge 202-203 is utilized to identify a new triangle 202,203,204 and the process is then repeated for each successive triangle until eventually another boundary edge 204-205 is reached.

Thus in the case of the illustration of FIG. 11 the points intersection 208-212 of the following edges with a plane 206 would be calculated: 200-201, 201-202, 202-203, 203-204 and 204-205. Thus in this way a series of points 208-212 lying within the plane 206 can be established and an approximation of the surface within that plane can then be calculated by determining a set of edges connecting the identified points 208-212 of intersection with the plane 206.

Returning to FIG. 10, after this intersection 208-212 of surface with a first plane 206 has been determined, the computer 5 then (S10-4) repeats the same processing of steps (S10-2-10-3) using a second plane including the plane for which the point of intersection has been determined. In this embodiment in the case of a ray at the centre of a beam of radiation this alternative ray is selected so as to form an angle of approximately 30° relative to the first plane 206. FIG. 12 is an illustration of a first and second planes 206, 214 and lines representing the portion of a surface including within the selected planes calculated in the manner described above.

By definition the intersection of these two planes will necessarily include the path of the ray being modelled. The point of intersection of this ray with the model surface can therefore be identified by the intersection 215 between the lines 208-212, 216 determined as representing the surface of the model lying within in the planes 206, 214. Where due to approximations these two lines do not coincide at a point 215, the closest point between the two lines 208-212, 216 can used as an approximation of the position 215 on the surface which corresponds to the intersection of the ray with the generated model.

Once the point 215 of intersection of the surface with the ray has been determined, a focus to skin distance can then be calculated by determining the distance of the identified point from the iso-centre 166 using conventional techniques and then subtracting this distance from the fixed distance between the iso-centre 166 and the focus positions of the radiation beam 165.

In addition to storing data representative of the focus to skin distance, the same technique described above can be utilized to calculate the points of intersection of a number of rays defining the outside edges of a beam of radiation. An outline of the edge of the irradiated surface at any particular time within the treatment can then be calculated by connecting the determined points of intersection for the rays. By calculating the extent of radiation at various times within the treatment, a record can be generated of the areas of the surface which have been irradiated. This information can be used in later treatments so as to avoid re irradiating the same areas of the surface of a patient.

Monitoring a Patient's Breathing

A generated model can also be used to monitor a patient's breathing cycle. This monitoring can in turn be utilised to activate the gating of the treatment apparatus 6 so as to irradiate a patient at a predetermined point within the breathing cycle, thereby reducing the invariability of the location of which radiation is administered.

In theory, when monitoring a patient's breathing, the movement of a single point on the surface of the patient should be followed. In order to monitor the breathing cycle in this way, it is necessary to determine which position in the model for separate frames corresponds to the same point of the surface at different times. Such point tracking is difficult and requires significant processing power if it is to be achieved within a time scale suitable for adjusting the activation of a treatment apparatus 6.

The applicants have determined that it is possible to obtain satisfactory monitoring of a patient's breathing without precisely tracking the movement of a single point on the surface of a patient. As a first approximation, it can be assumed that any movement arising from breathing takes place in a direction normal to the surface of the patient at that point. Further for the purposes of monitoring the breathing cycle it is not necessary to determine the exact distances a point moves. An acceptable approximation is only to consider movement within a selected plane close to or including the identified normal. Instead of attempting to track a point in three dimensions, it is therefore satisfactory to monitor the movement of a point within a selected plane being the projection of the selected point in that plane.

In this embodiment when a patient's breathing is to be monitored, after a complete model of the patient for a first frame has been generated the area of images used to generate the portion of a patient being monitored is first determined and all subsequent processing involves generating models and model contours only for that area.

For the selected point being monitored, a contour being the intersection of a portion of that model including the point with a selected plane is first calculated in the manner previously described. A transform necessary to align a vector in the plane, normal to the contour at the point being monitored, with the y co-ordinate axis is then calculated. For successive frames after a model of the area being monitored has been generated and co-ordinate data for a contour for the intersection of the model with a selected plane calculated the calculated transform is then applied to the co-ordinate data for the contour. A breathing measurement can then be made by monitoring the y co-ordinate value for the contour for the x co-ordinate corresponding to the position of the selected point in the initial frame transformed by the calculated transform.

Modifications and Amendments

Although in the above embodiment, a specific method for calibrating the co-ordinates for a model with the iso centre of a treatment room has been described, it would be appreciated that other methods can also be utilised. In particular, instead of taking multiple images of a calibration plate a single image of a calibration plate with a target placed as accurately as possible to line up with the light field of the gantry and hence at the iso centre could be utilised. Such a simplified calibration may not necessarily be as accurate as the method previously described. Such a system could however, be utilised as a simple check to ensure that the camera rig positions have not been modified since last time a full calibration of the system had occurred.

It will be appreciated that whereas all of the measurements described above such as calculating an FSD measurement or the area of irradiated skins surface could be calculated utilizing a complete model of a patient, quicker processing can be achieved by identifying the portion of a model representing an area of interest and determining measurements for that area by only processing image data or model data for that area.

As described above usually the most stable point in the breathing cycle for capturing and utilizing reference surfaces is when a patient has just expired and before the patient begins to inhale once again. For this reason it is normally preferable to position patients using reference surfaces captured at this point in the breathing cycle.

Some diagnostic or planning data such as CT data is obtained over a number of breathing cycles. When determining the relative location of points identified in the planning or diagnostic data relative to the surface of a patient, it is preferable to determine how a calculated surface generated directly from the diagnostic or planning data matches with a generated image surface in the middle of the breathing cycle.

When using such data initially a patient could be monitored to obtain model surfaces for a number of frames and a frame representing the middle of the breathing cycle could be identified. Patient positioning in an initial treatment session could then be achieved by aligning a model surface of a patient representing the middle of the breathing cycle and the calculated surface for the captured planning data. A model surface of the patient in the calculated position captured just before the patient begins to inhale once again could then be determined and this model data could then be utilized to position the patient in subsequent treatment sessions.

In the system described above estimates of the co-ordinates of the centres of circles appearing on the surface of a calibration sheet are described as being identified on the basis of grey scale values where the colour of the circle is associated with a high grey scale value and the colour of the background corresponding to the calibration sheet is associate with a low grey scale value. It will be appreciated that such a result could be achieved by selecting the colouring of the calibration sheet so that this result was achieved. Alternatively, the colour selected for the circles on the calibration sheet could be selected to give rise to lower values than the background and image data could then be inverted prior to processing.

In the above described embodiment the determination of the positions of circle centres is described solely on the basis of processing grey scale images. It will be appreciated that initial estimates of circle centre positions could be calculated by thresholding the grey scale images and utilising the generated binary images to identify the initial estimate locations for the circle centres. Improved estimates could then be achieved by processing the grey scale images to take advantage of the additional information in such images to improve the accuracy of the circle centre estimates.

Although in the above described embodiment a system for monitoring breathing has been described in which a calculated transform is applied to generated co-ordinate data for a contour, it will be appreciated that as an alternative the calculated transform could be applied to the generated model data and contour data could then be derived from model data to which the calculated transform had been applied.

Alternatively, instead of monitoring breathing in the manner described in detail in the embodiment, a rough measurement could be achieved by calculating FSD measurements for the patient at different times and the variation of the FSD measurement could be taken to indicate when a patient inhales and exhales.

Although the embodiments of the invention described with reference to the drawings comprise computer apparatus and processes performed in computer apparatus, the invention also extends to computer programs, particularly computer programs on or in a carrier, adapted for putting the invention into practice. The program may be in the form of source or object code or in any other form suitable for use in the implementation of the processes according to the invention. The carrier can be any entity or device capable of carrying the program.

For example, the carrier may comprise a storage medium, such as a ROM, for example a CD ROM or a semiconductor ROM, or a magnetic recording medium, for example a floppy disc or hard disk. Further, the carrier may be a transmissible carrier such as an electrical or optical signal which may be conveyed via electrical or optical cable or by radio or other means.

When a program is embodied in a signal which may be conveyed directly by a cable or other device or means, the carrier may be constituted by such cable or other device or means.

Alternatively, the carrier may be an integrated circuit in which the program is embedded, the integrated circuit being adapted for performing, or for use in the performance of, the relevant processes.

The invention claimed is:

1. A method of processing a wire mesh computer model of a surface comprising a plurality of triangles defined by vertices connected by edges to generate data identifying a set of points of intersection of said wire mesh model with a plane, the method comprising:
   (i) identifying pairs of vertices connected by edges at the boundary of said wire mesh model which lie on opposite sides of said plane;
   (ii) selecting one of said identified boundary edges as an initial edge for processing;
   (iii) storing data identifying the point of intersection of the selected edge with said plane;
   (iv) identifying the vertex of said wire mesh model connected to both of the vertices of said selected edge;
   (v) determining which of said vertices of said selected edge lies on the opposite side of said plane to said identified vertex;
   (vi) selecting as the next edge to process the edge of the triangle connecting said identified vertex and the vertex of said processed edge lying on the opposite side of said plane; and
   (vii) determining whether said newly selected edge corresponds to an edge identified as a boundary edge and if not repeating steps (iii)-(vi), wherein if the identified set of points of intersection are on a surface of a patient, the wire mesh computer model is implemented in a computer of a patient positioning system to establish where a ray from a centre of a radiation beam impinges on the surface of the patient so that the focus to skin distance can be calculated.

2. The method in accordance with claim 1 wherein identifying pairs of vertices connected by edges at the boundary of said wire mesh model which lie on opposite sides of said plane comprises:
storing data identifying co-ordinates of pairs of vertices corresponding to boundary edges of a wire mesh computer model; and
identifying as boundary edges pairs of vertices of which lie on opposite sides of said plane by identifying pairs of vertices where the dot product of the difference between the co-ordinates of an identified point on the plane and co-ordinates of said vertices and a vector normal to said plane are of different signs.

3. The method in accordance with claim 1 wherein determining which of said vertices of said selected edge lies on the opposite side of said plane to said identified vertex comprises identifying the vertex for which the dot product of a normal vector to said plane and the difference between the co-ordinates of an identified point on the plane and co-ordinates of said vertex has different sign to the dot product of a normal vector to said plane and the difference between the co-ordinates of an identified point on the plane and co-ordinates of said identified vertex.

4. A method of identifying the intersection of a vector with a wire mesh model comprising a plurality of triangles defined by vertices connected by edges, the method comprising:
processing a wire mesh computer model of a surface to generate data identifying a set of points of intersection of said wire mesh model with a first plane including said vector by:
(i) identifying the pairs of vertices connected by edges at the boundary of said wire mesh model which lie on opposite sides of said first plane;
(ii) selecting one of said identified boundary edges as an initial edge for processing;
(iii) storing data identifying the point of intersection of said selected edge with said first plane;
(iv) identifying the vertex of said wire mesh model connected to both of the vertices of said selected edge;
(v) determining which of said vertices of said selected edge lies on the opposite side of said first plane to said identified vertex;
(vi) selecting as the next edge to process the edge of said triangle connecting said identified vertex and the vertex of said processed edge lying on the opposite side of said first plane; and
(vii) determining whether said newly selected edge corresponds to an edge identified as a boundary edge and if not repeating steps (iii)-(vi);
processing said wire mesh computer model of a surface to generate data identifying a set of points of intersection of said wire mesh model with a second plane including said vector by:
(i) identifying the pairs of vertices connected by edges at the boundary of said wire mesh model which lie on opposite sides of said second plane;
(ii) selecting one of said identified boundary edges as an initial edge for processing;
(iii) storing data identifying the point of intersection of said selected edge with said second plane;
(iv) identifying the vertex of said wire mesh model connected to both of the vertices of said selected edge;
(v) determining which of said vertices of said selected edge lies on the opposite side of said second plane to said identified vertex;
(vi) selecting as the next edge to process the edge of said triangle connecting said identified vertex and the vertex of said processed edge lying on the opposite side of said second plane; and
(vii) determining whether said newly selected edge corresponds to an edge identified as a boundary edge and if not repeating steps (iii)-(vi); and
determining the closest point of intersection of a set of edges connecting consecutive points in said generated sets of points for said first and second planes, wherein if the identified set of points of intersection are on a surface of a patient, the wire mesh computer model is implemented in computer of a patient positioning system to establish where a ray from a centre of a radiation beam impinges on the surface of the patient so that the focus to skin distance can be calculated.

5. The method in accordance with claim 4 further comprising:
determining the distance between said determined closest point of intersection and a predetermined point and outputting data identifying said distance.

6. A method of generating data representative of the extent to which a beam of radiation irradiates the surface of the patient comprising:
generating a wire mesh model of the surface of the patient;
determining for a plurality of vectors identifying expected paths of a modelled beam of radiation, the points of intersection of said vectors with said generated surface in accordance with claim 4; and
determining the area of said modelled surface enclosed by a boundary connecting said determined points of intersection.

7. The method in accordance with claim 6 further comprising:
determining the extent radiation of the patient at a plurality of different times during a treatment; and
generating a model representing the sum of the extent of radiation throughout said period.

8. The method in accordance with claim 7 further comprising:
determining an estimate of dose of radiation at each of said times wherein said generated model identifies the estimated total dose of radiation in said areas of extent.

9. The method in accordance with claim 7 comprising generating a texture rendered representation of said surface texture rendered utilising said generated data representing the sum of the extent of radiation throughout said period.

10. An apparatus for processing a wire mesh computer model of a surface comprising a plurality of triangles defined by vertices connected by edges to generate data identifying a set of points of intersection of said wire mesh model with a plane comprising:
a model store storing co-ordinate data representing a wire mesh model;
a surface processor operable to process stored model data to identify the pairs of vertices connected by edges at the boundary of said wire mesh model which lie on opposite sides of a plane;
a vertex processor operable to sequentially process pairs of vertices corresponding to edges in a wire mesh model by:
identifying the point of intersection of a selected edge with a plane;
identifying the vertex of said wire mesh model connected to both of the vertices of said selected edge;

determining which of said vertices of said selected edge lies on the opposite side of said plane to said identified vertex; and selecting as the next edge to process the edge of the triangle connecting said identified vertex and the vertex of said processed edge lying on the opposite side of said plane, wherein if the apparatus is included in a patient positioning system, and if the identified set of points of intersection are on a surface of a patient, the wire mesh computer model is implemented in the apparatus to establish where a ray from a centre of a radiation beam impinges on a surface of a patient so that the focus to skin distance can be calculated.

11. The apparatus in accordance with claim 10 wherein a surface processor operable to process stored model data comprises:

a data store operable to store data identifying co-ordinates of pairs of vertices corresponding to boundary edges of a wire mesh computer model; and a processor operable to identify as boundary edges the vertices of which lie on opposite sides of said plane by identifying pairs of vertices where the dot product of the difference between the co-ordinates of an identified point on the plane and the co-ordinates of said vertices and a vector normal to said plane are of different signs.

12. The apparatus in accordance with claim 10 wherein said vertex processor is operable to determine which of said vertices of a selected edge lie on the opposite side of said plane to said identified vertex by identifying the vertex for which the dot product of a normal vector to said plane and the difference between the co-ordinates of an identified point on the plane and the co-ordinates of vertex has different sign to the dot product of a normal vector to said plane and the difference between the co-ordinates of an identified point on the plane and the co-ordinates of identified vertex.

13. An apparatus for identifying the intersection of a vector with a wire mesh model comprising:

a model store storing co-ordinate data representing a wire mesh model;

a surface processor operable to process model data stored in said data store to identify the pairs of vertices connected by edges at the boundary of said wire mesh model which lie on opposite sides of a plane;

a vertex processor operable to sequentially process pairs of vertices corresponding to edges in a wire mesh model by:
identifying the point of intersection of a selected edge with a plane;
identifying the vertex of said wire mesh model connected to both of the vertices of the selected edge;
determining which of the vertices of the selected edge lies on the opposite side of said plane to said identified vertex; and
selecting as the next edge to process the edge of the triangle connecting said identified vertex and the vertex of said processed edge lying on the opposite side of said plane; and an intersection determination module operable to determine the closest point of intersection of a set of edges connecting consecutive points in sets of points of intersection determined by said vertex processor for a first and a second plane, wherein if the apparatus is included in a patient positioning system, and if the identified set of points of intersection are on a surface of a patient, the wire mesh computer model is implemented in the apparatus to establish where a ray from a centre of a radiation beam impinges on the surface of the patient so that the focus to skin distance can be calculated and so that points on the surface to which the outer edge of the radiation beam extend can be identified.

14. The apparatus in accordance with claim 13 further comprising:

a distance determination module operable to determine the distance between said determined closest point of intersection determined by said intersection determination module and a predetermined point and outputting data identifying said distance.

15. An apparatus for generating data representative of the extent to which a beam of radiation irradiates the surface of a patient comprising:

a model generator operable to generate a wire mesh model of the surface of a patient;

a model store storing co-ordinate data representing a wire mesh model;

a surface processor operable to process stored model data to identify the pairs of vertices connected by edges at the boundary of said wire mesh model which lie on opposite sides of a plane;

a vertex processor operable to sequentially process pairs of vertices corresponding to edges in a wire mesh model by:
identifying the point of intersection of a selected edge with a plane;
identifying the vertex of said wire mesh model connected to both of the vertices of said selected edge;
determining which of said vertices of said selected edge lies on the opposite side of said plane to said identified vertex; and
selecting as the next edge to process the edge of the triangle connecting said identified vertex and the vertex of said processed edge lying on the opposite side of said plane;

an intersection determination module operable to determine the closest point of intersection of a set of edges connecting consecutive points in sets of points of intersection determined by said vertex processor for a first and a second plane; and an area calculation module operable to determine the area of said modelled surface enclosed by a boundary connecting a set of determined points of intersection determined by said intersection determination module, wherein the apparatus is included in a patient positioning system, wherein the identified sets of points of intersection are on a surface of a patient, and wherein the model generator and the area calculation module are implemented to calculate the extent of radiation.

16. The apparatus in accordance with claim 15 wherein said:

area calculation module is operable to determine the extent radiation of a patient at a plurality of different times during a treatment said model generator further being operable to generate a model representing the sum of the extent of radiation throughout said period utilising said calculations of area made by said area calculation module.

17. The apparatus in accordance with claim 16 wherein said model generator is operable to generate a texture rendered representation of said surface texture rendered utilising said calculated data representing the sum of the extent of radiation throughout said period.

18. A computer readable storage medium storing computer interpretable-instructions which when interpreted by a programmable computer storing a wire mesh computer model of a surface comprising a plurality of triangles defined by vertices connected by edges, cause the programmable computer to perform a method to generate data identifying a set of points of intersection of said wire mesh model with a plane, the method comprising:

(i) identifying pairs of vertices connected by edges at the boundary of said wire mesh model which lie on opposite sides of said plane;

(ii) selecting one of said identified boundary edges as an initial edge for processing;

(iii) storing data identifying the point of intersection of the selected edge with said plane;

(iv) identifying the vertex of said wire mesh model connected to both of the vertices of said selected edge;

(v) determining which of said vertices of said selected edge lies on the opposite side of said plane to said identified vertex;

(vi) selecting as the next edge to process the edge of the triangle connecting said identified vertex and the vertex of said processed edge lying on the opposite side of said plane; and (vii) determining whether said newly selected edge corresponds to an edge identified as a boundary edge and if not repeating steps (iii)-(vi).

* * * * *